(12) United States Patent
Akita

(10) Patent No.: US 6,629,989 B2
(45) Date of Patent: Oct. 7, 2003

(54) PHOTOTHERAPY DEVICE FOR PRESSURE PAIN POINT THERAPY AND TRIGGER POINT THERAPY

(75) Inventor: Satoshi Akita, Nagaokakyo (JP)

(73) Assignee: Shimadzu Corporation, Kyoto (JP)

( * ) Notice: Subject to any disclaimer, the term of this patent is extended or adjusted under 35 U.S.C. 154(b) by 0 days.

(21) Appl. No.: 09/978,588

(22) Filed: Oct. 18, 2001

(65) Prior Publication Data

US 2003/0078637 A1 Apr. 24, 2003

(51) Int. Cl.[7] ................................................. A61H 5/06
(52) U.S. Cl. ............................................ 607/90; 607/88
(58) Field of Search .......................... 607/88, 89; 606/2, 606/9, 13; 128/907

(56) References Cited

U.S. PATENT DOCUMENTS

| | | | | |
|---|---|---|---|---|
| 4,232,678 A | * | 11/1980 | Skovajsa | 128/907 |
| 4,535,784 A | * | 8/1985 | Rohlicek et al. | 128/907 |
| 5,024,236 A | * | 6/1991 | Shapiro | 128/907 |
| 5,304,207 A | * | 4/1994 | Stromer | 607/88 |
| 5,464,436 A | * | 11/1995 | Smith | 606/13 |
| 5,957,960 A | * | 9/1999 | Chen et al. | 607/88 |
| 6,187,029 B1 | * | 2/2001 | Shapiro et al. | 607/88 |
| 6,306,160 B1 | * | 10/2001 | Nidetzky | 606/2 |
| 6,443,978 B1 | * | 9/2002 | Zharov | 607/88 |

* cited by examiner

*Primary Examiner*—Lee Cohen
*Assistant Examiner*—H. M. Johnson
(74) *Attorney, Agent, or Firm*—Kanesaka & Takeuchi

(57) ABSTRACT

A phototherapy device for a pressure pain point therapy or trigger point therapy includes one LED as a light source for therapy, and a projection portion projecting from a front surface of a case to be located along an optical axis of the LED. The projection portion is pressed against a user's body to search a pressure pain point or trigger point, and the LED is turned on after searching the point, so that a photic stimulation can be securely provided to the pressure pain point or trigger point with a clear difference between the point and a region around the point, to thereby easily carry out the pressure pain point therapy or the trigger point therapy.

3 Claims, 3 Drawing Sheets

PHOTOTHERAPY DEVICE FOR PRESSURE PAIN POINT THERAPY AND TRIGGER POINT THERAPY

BACKGROUND OF THE INVENTION AND RELATED ART STATEMENT

The present invention relates to a phototherapy device, and more particularly, it relates to a phototherapy device which is suitable for a pressure pain point therapy or trigger point therapy as a household health therapy device.

It has been known that a pressure pain point where pain is felt by applying pressure thereto, and a trigger point as a pressure pain point which causes related pain, exist in a skeletal muscle, a tendon of a skeletal muscle, articular capsule, ligament, periosteum, skin or the like, and by stimulating these points, an effective therapy for pain can be carried out. As a method of stimulating the pressure pain point or trigger point, stimulation by injection of medicine or acupuncture has been practiced as the trigger point therapy, and experimentally, an irradiation of low power laser has been carried out.

However, in the conventional trigger point therapy as described above, although the therapy is effective, only an expert can perform the therapy, and it is impossible to perform the therapy at home.

Accordingly, an object of the invention is to provide a photo or light therapy device for a pressure pain point therapy and a trigger point therapy which can easily and safely stimulates the pressure pain point or trigger point at home, to thereby achieve the same effect as in the conventional trigger point therapy.

Further objects and advantages of the invention will be apparent from the following description of the invention.

SUMMARY OF THE INVENTION

To achieve the aforementioned object, the present invention provides a phototherapy device for a pressure pain point therapy or a trigger point therapy to be used by contacting the device on a user's body. According to the first aspect of the invention, in the phototherapy device for a pressure pain point therapy or trigger point therapy of the invention, a light source for therapy is formed of only one LED (light emitting diode), and a projection portion for searching a pressure pain point or trigger point projects from a case for accommodating or holding the LED, which is located on an optical axis of the LED.

According to the second aspect of the invention, in the phototherapy device for a pressure pain point therapy or trigger point therapy as stated above, the projection portion can be formed on a package itself of the LED, which projects from the front surface of the case.

According to the third aspect of the invention, it is preferable to provide a display light for confirming an operation on a surface of the case, which is different from the surface from which the projection portion projects.

Further, according to the fourth aspect of the invention, in case the present invention is used as a therapy or treatment of the joint, a projecting amount or length of the projection portion from the front surface of the case is preferably set in a range from 0.3 mm to 3 mm. Also, according to the fifth aspect of the invention, in case the present invention is used as a treatment of a stellate ganglion, the projecting length of the projection portion from the front surface of the case is preferably set in a range from 10 mm to 30 mm.

Incidentally, although an output wavelength of the LED of the invention is not specially limited, infrared ray including near infrared, and visible light can be preferably used.

In the present invention, only one LED as an inexpensive point light source is used, and by locally irradiating an output light of the LED to the pressure pain point or trigger point, a stimulation is given to these points. At the same time, the pressure pain point or the trigger point to which the light should be irradiated can be easily found by using the projection portion projecting from the front surface of the case on the optical axis of the LED, and a user can proceed to a phototherapy immediately.

Namely, in case the light source is formed of only one LED, if the output light of the LED is locally irradiated to the portion of the user's body, an apparent difference in an amount of irradiation of the light appears between an irradiated portion of the user's body and an adjacent region around the irradiated portion, so that the effective photic stimulation can be provided to the irradiated portion. Accordingly, it has been proved that there is a high therapeutic effect with respect to the pressure pain point or trigger pain point as described later.

Here, in the LED used as the light source for therapy in the invention, there can be utilized an output light power which has a large broadening angle in the outgoing light and is the same as that of a laser used for the lower power laser therapy. Namely, it has been confirmed that in both laser and LED, after light for the therapy is irradiated onto the human body, the light is scattered to tissues inside the body, so that the light is largely supplied in substantially the same state. Therefore, even if the LED is used as the light source, the same effect as in the lower power laser therapy can be expected.

Then, by utilizing the fact that the pressure pain point or the trigger point is a portion where a pain is felt apparently different from that around the portion when the portion is pressed, if the projection portion projecting from the front surface of the case along the optical axis of the LED is pushed against the body and moved, the pressure pain point or the trigger point as the point which needs the therapy can be easily found by relying upon the pain felt. Then, the user can proceed to the phototherapy immediately.

In the second aspect of the invention, it is useful to utilize the package of the LED as the projection portion in view of simplifying the structure of the phototherapy device to lower the cost thereof.

Also, in the phototherapy device of the invention, the LED as the light source of the device faces the front surface of the human body in use, and in addition, in case the near infrared light or the like is used as the LED, turning on and off of the light can not be perceived by the human eyes. Thus, as in the third aspect of the invention, it is extremely preferable in view of the safety to provide a display or the like on a surface of the case different from the surface from which the projection portion projects, that is, another surface different from the surface in which the LED is disposed, to thereby realize the condition of tuning on and off.

Then, in case the phototherapy device of the invention is used for a treatment of the joint, it is effective in searching a pressure pain point or trigger point existing in soft tissues among complicated hard and soft tissues to form such that the projecting amount of the projection portion from the front surface of the case is 0.3 mm to 3 mm. Also, in case the phototherapy device of the invention is used for a treatment of the stellate ganglion, it is very convenient in searching the pressure pain point or the trigger point existing in an inner side of a muscle near a neck bone to form such that the projecting amount of the projection portion from the front surface of the case is 10 mm and 30 mm.

Incidentally, in the present invention, the projection amount or length of the projection portion from the front surface of the case is not limited to the aforementioned range of 0.3 mm to 3 mm and the range of 10 mm to 30 mm, and in case a portion other than the joint or stellate ganglion, for example, a muscle, is treated, it has been confirmed that the phototherapy device is handy if the projection portion projects in a length of 3 mm to 10 mm.

DETAILED DESCRIPTION OF PREFERRED EMBODIMENTS

Hereunder, preferred embodiments of the invention will be explained with reference to the accompanied drawings.

Figure 1:
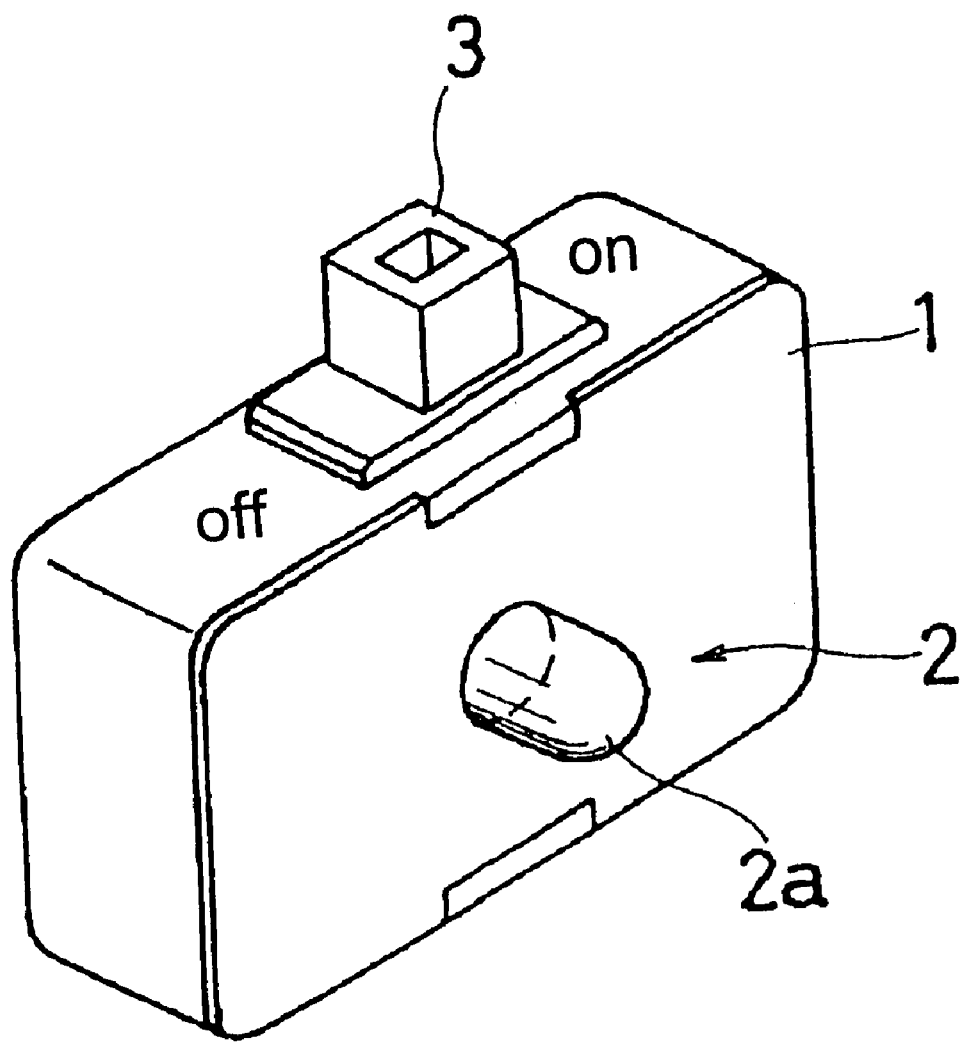
FIG. 1 is a perspective view showing an appearance of an embodiment of the invention.
Figure 2B:
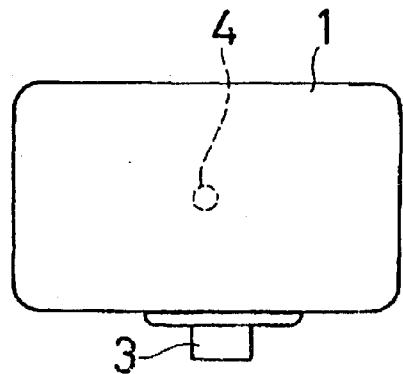
FIG. 2(B) is a rear view thereof.
Figure 2A:
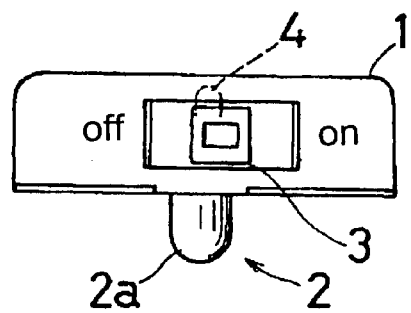
FIG. 2(A) is a plan view of the embodiment.
Figure 2C:
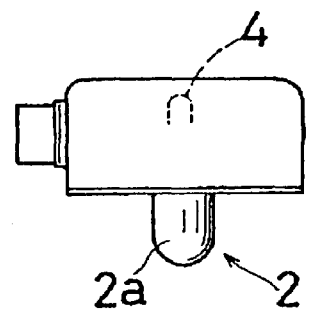
FIG. 2(C) is a right side view thereof.

FIG. 1 is a perspective view of an embodiment of the invention; FIG. 2(A) is a plan view showing an upper side thereof; FIG. 2(B) is a rear view thereof ; and FIG. 2(C) is a right side view thereof. Also, FIG. 3 is a circuit diagram showing an electrical structure of the embodiment of the invention.

On one surface of a case 1 having a shape of a flat, substantially rectangular parallelepiped, there is disposed one near infrared light emitting diode 2 (hereinafter referred to as near infrared LED) as a light emitting diode for therapy. The near infrared LED 2 is stored inside a package 2a, which is integrally formed with a lens and made of a translucent resin. In a state that the package 2a projects in several millimeters, for example, in 5 mm, from a front surface of the case 1, the package 2a is fixed on a base, not shown, stored inside the case 1.

In the case 1, on a side surface with respect to the surface in which the near infrared LED 2 is provided, there is provided a switch 3 for turning on and off the near infrared LED 2. Also, an LED (light emitting diode) 4 for monitoring, which outputs visible light, such as red LED, is stored inside the case 1, and the LED 4 for monitoring is disposed such that outgoing light from the LED 4 for monitoring is visible through the case 1 from a rear surface side with respect to the surface of the case 1 where the near infrared LED 2 is disposed.

Figure 3:
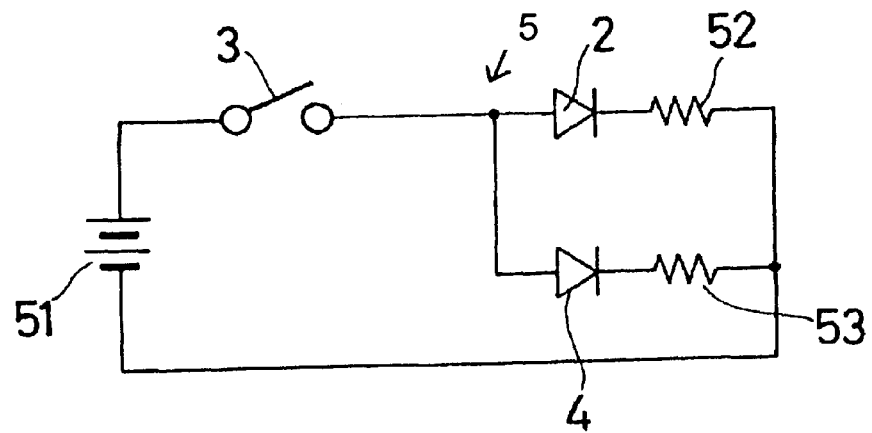
FIG. 3 is a circuit diagram showing an electrical structure of the embodiment.

Also, a drive circuit 5, shown in FIG. 3, which includes the switch 3 described above is stored inside the case 1, and by operating the switch 3, the near infrared LED 2 and the LED 4 for monitoring are simultaneously turned on or off. Namely, the drive circuit 5 includes a power supply battery 51, and in the condition that the near infrared LED 2 and the LED 4 for monitoring are respectively connected to adequate resistors 52 and 53 in series, the near infrared LED 2 and the LED 4 for monitoring are connected to the power supply battery 51 in parallel. Also, the switch 3 is interposed between the power supply battery 51 and the respective LEDs 2 and 4.

Next, an example of a method of using the embodiment of the invention will be explained.

Firstly, a pressure pain point or trigger point is searched. In general, since a place where the pressure pain point or trigger point exists is roughly known according to a portion of the pain and a state of the pain, in searching the point, a distal end of the package 2a, which projects from the case 1 to form a convex portion, of the near infrared LED 2, is pressed and moved adequately in the vicinity of the roughly known place, to thereby search a place where the pain is felt most strongly in the vicinity of the roughly known place. When the place where the pain is felt most strongly is found, while the case 1 is positioned as it is, the switch 3 is operated to turn on the near infrared LED 2 for a predetermined period of time, so as to apply the therapy.

After the therapy as described above, it is searched by the same method as described above whether there is another point where the pain is concentrated, and if such a point is found, the point is treated by the same method as described above.

The remarkable point in the embodiment of the invention is that the package 2a of the near infrared LED 2 projects from the case 1. Accordingly, the case 1 includes the projection portion projecting along an optical axis of the near infrared LED 2 as the light source for therapy, and the projection portion formed of the package 2a of the near infrared LED 2 can be used for searching the pressure pain point and the trigger point. Also, after searching, it is possible to provide the photo or light therapy as it is. Moreover, operations from the searching to the therapy are extremely simple, so that the even if a non-expert ordinary person can easily carry out the pressure pain point therapy or the trigger point therapy.

In explaining the monitored results obtained in using the embodiment of the invention, the therapeutic effect was 90.4% in the total efficiency rate in case a doctor used the phototherapy device of the invention. In case a general person who does not have medical knowledge used the phototherapy device of the invention, the therapeutic effect was 74% in the total efficiency rate. Especially, in regard to the symptoms of the arthralgia, sprain, and thecitis, more than 80% in the total efficiency rate was obtained even if the ordinary person used the device.

Incidentally, although the near infrared LED is used as the light source for the therapy in the aforementioned embodiment, the present invention is not limited thereto, and by using the infrared having a longer wavelength and LED outputting the visible light, the same effects can be obtained.

Also, although the package 2a of the LED 2 for therapy projects from the case 1 such that the package 2a itself constitutes the projection portion for searching the pressure pain point or the trigger point in the aforementioned embodiment, a protective cover made of silicone rubber or the like, which is available in the market, may be attached to the package 2a of the LED 2 for therapy such that the protective cover constitutes the projection portion for searching the pressure pain point or trigger point. Alternatively, in case the LED 2 for therapy is required to project by exceeding the size of the package 2a, there can be adopted a structure in which a step portion projecting from the front surface of the case 1 is provided so as to fix the LED 2 for therapy on the step portion.

Further, in the present invention, as the projection portion which projects from the case 1 to search the pressure pain point and the trigger point, the following modified example can be employed.

Figure 4:
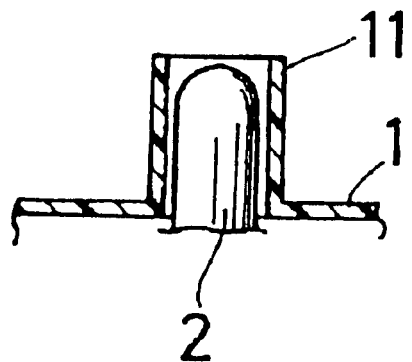
FIG. 4 is a sectional view showing a main structure of another embodiment of the invention.

Namely, in an example of FIG. 4 showing a main part thereof in section, a cylindrical portion 11, which has an open distal end and covers a periphery of the LED 2 for therapy, projects on an optical axis of the LED 2 for therapy.

Figure 5:
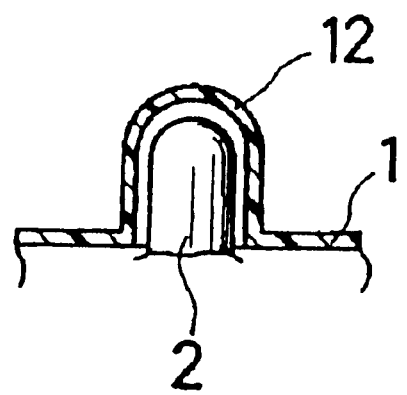
FIG. 5 is a sectional view showing a main structure of a further embodiment of the invention.

Also, in an example of FIG. 5 showing a main part thereof in section, a dome portion 12 covering the LED 2 for therapy is integrally formed with the case 1 to project along the optical axis of the LED 2 for therapy, and the dome portion 12 is made of a material having a transparency with respect to the outgoing light from the LED 2 for therapy.

The cylindrical portion 11 and the dome portion 12 described above are also effective in searching the pressure pain point or the trigger point as in the aforementioned embodiment, and they are the same as the aforementioned embodiment in that the user can apply the phototherapy right after searching these points.

Also, in using the phototherapy device of the invention, the device can be pushed against the therapy point by hand, or can be pushed against the therapy point by a supporter to be fixed thereto. Furthermore, the phototherapy device can be fixed to an exclusive band or holder, and the device can be fixed to a human body by the band or holder.

Furthermore, in the aforementioned embodiment, it is explained with the example that the drive circuit 5 including the power supply battery 51 is accommodated in the case 1. However, the power supply battery 51 can be completely confined inside the case 1 by sealing the case 1, or a lid freely capable of opening and closing may be provided at the case 1 so that the power supply battery 51 can be replaced. Also, in the present invention, without providing the power supply battery in the case 1, there can be adopted a structure in which an external power supply is used and connected to the case 1.

Still further, in the present invention, it is needless to say that any additional function for improving convenience in use, such as a timer function provided in the drive circuit for the LED 2 for therapy, can be added freely.

According to the present invention, a single LED is provided as a light source for phototherapy, and also, there is provided the projection portion projecting along the optical axis of the LED from the front surface of the case which holds or accommodates the LED. Therefore, by pressing the projection portion against the user's body, the pressure pain point or the trigger point can be easily searched, and the user can proceed to the phototherapy right after searching these points.

Also, in case of the phototherapy, light is locally irradiated to the predetermined portion, to thereby provide an effective photic-stimulation by having an apparent difference in the amount of irradiation of light between the predetermined portion and a region around the predetermined portion, resulting in achieving the same effect as in the lower power laser therapy. Also, an ordinary person who does not have medical knowledge can easily carry out the pressure pain therapy or trigger point therapy effectively by using the phototherapy device of the invention.

While the invention has been explained with reference to the specific embodiments of the invention, the explanation is illustrative and the invention is limited only by the appended claims.

What is claimed is:

1. A phototherapy device for a pressure pain point therapy and trigger point therapy, comprising:

a light source for therapy formed of a light emitting diode, a case for holding the light emitting diode therein, said case having a flat front surface, and rear and side surfaces, a projection portion for searching one of a pressure pain point and a trigger point, said projection portion projecting from the flat front surface of the case in a range from 0.3 mm to 3 mm to be used for a treatment of a joint and located along an optical axis of the light emitting diode, said projection portion being formed of a translucent resin and integrally formed with a lens to form a package so that the light emitting diode is located in the package to eject light therethrough, a display light for checking an operation of the light emitting diode, said display light being provided inside the case behind the projection portion so that light from the display light can be seen through the rear surface of the case opposite to the front surface, and a switch electrically connected to the light source and the display light and disposed on the side surface of the case for operating the light emitting diode and the display light.

2. A phototherapy device according to claim 1, wherein said case has a projection for covering a periphery of the light emitting diode to constitute the projection portion.

3. A phototherapy device for a pressure pain point therapy and trigger point therapy, comprising:

a light source for therapy formed of a light emitting diode, a case for holding the light emitting diode therein, and said case having a flat front surface, and rear and side surfaces.

a projection portion for searching one of a pressure pain point and a trigger point, said projection portion projecting from the flat front surface of the case in a range from 10 mm to 30 mm to be used for a treatment of stellate ganglion and located along an optical axis of the light emitting diode, said projection portion being formed of a translucent resin and integrally formed with a lens to form a package so that the light emitting diode is located in the package to eject light therethrough, a display light for checking an operation of the light emitting diode, said display light being provided inside the case behind the projection portion so that light from the display light can be seen through the rear surface of the case opposite to the front surface, and a switch electrically connected to the light source and the display light and disposed on the side surface of the case for operating the light emitting diode and the display light.

* * * * *